United States Patent [19]

Ohsumi et al.

[11] Patent Number: 4,837,242
[45] Date of Patent: Jun. 6, 1989

[54] THIAZOLES AND PYRAZOLES AS FUNGICIDES

[75] Inventors: Tadashi Ohsumi; Kazunori Tsushima; Sumio Nishida; Kiyoto Maeda, all of Hyogo; Tadashi Ooishi, Saitama; Noritada Matsuo, Hyogo, all of Japan

[73] Assignee: Sumitomo Chemical Company, Limited, Osaka, Japan

[21] Appl. No.: 139,607

[22] Filed: Dec. 30, 1987

[30] Foreign Application Priority Data

Jan. 20, 1987 [JP] Japan .................................. 62-11666
Jan. 20, 1987 [JP] Japan .................................. 62-11667
Feb. 10, 1987 [JP] Japan .................................. 62-28574

[51] Int. Cl.$^4$ .................. A01N 43/78; C07D 277/04; C07D 231/10; C07D 277/18
[52] U.S. Cl. ................................ 514/365; 548/200; 548/378; 548/194; 514/406; 514/370; 514/407; 514/400
[58] Field of Search .................... 548/200, 378, 194; 514/400, 406, 365, 370, 407

[56] References Cited

FOREIGN PATENT DOCUMENTS 0086111 9/1983 European Pat. Off. ............ 548/200
0151866 5/1984 European Pat. Off. ............ 548/200
0199822 10/1985 European Pat. Off. ............ 548/200
1695968 11/1967 Fed. Rep. of Germany ...... 548/200
2701091 6/1977 Fed. Rep. of Germany ...... 548/200

OTHER PUBLICATIONS

Morrison et al., Textbook "Organic Chemistry", Allyn & Bacon, Inc., Boston, Mass. 1973, p. 665.
Chem Abstracts, vol. 107, No. 58665 (1987).
Chem Abstracts, vol. 102, No. 61951g (1985).
Patent Abstracts of Japan, vol. 5, #120 (1981).
Structure–Activity Relationships in a Series of . . . Carboxanilides: J. L. Huppatz: pp. 45–50.
Fungitoxicity and Structure Activity . . . Derivatives: Marten Snel et al; pp. 1164–1169.
C.A. 70 87799j Heterocyclic Compounds, Harrison, William A.; p. 343.
Pesticide Biochemistry & Physiology 5; G. A. White, et al: pp. 380–395.
Systemic Fungicides, The Synthesis of Certain Pyrazole Analogues of Carboxin: J. Huppatz: pp. 135–147.

Primary Examiner—Mary C. Lee
Assistant Examiner—Robert C. Whittenbaugh
Attorney, Agent, or Firm—Ladas & Parry

[57] ABSTRACT

Heterocyclic derivatives represented by the following formula have excellent preventive, curative and systemic controlling effects on various plant microbes.

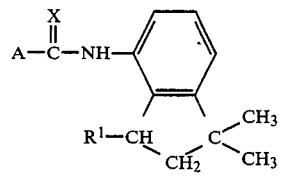

wherein $R^1$ represents a hydrogen atom or a methyl group, A represents

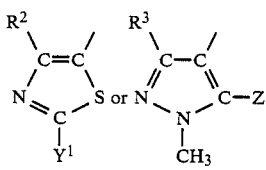

wherein $R^2$ represents a methyl group, an ethyl group or a trifluoromethyl group, $Y^1$ represents an amino group, a methyl group or a chlorine atom, $R^3$ represents a methyl group or a trifluoromethyl group and Z represents a hydrogen atom, a halogen atom or a methyl group and when A represents the formula:

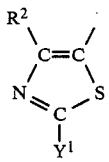

X represents an oxygen atom or sulfur atom and when A represents the formula:

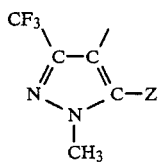

X represents a sulfur atom.

4 Claims, No Drawings

THIAZOLES AND PYRAZOLES AS FUNGICIDES

BACKGROUND OF THE INVENTION

The present invention relates to a heterocyclic derivative, a method for preparing the same and a fungicide containing the derivative as an active ingredient.

Fungicidal activity of some heterocyclic derivatives is reported in Chem. Abstr. 70 8799j (S. African 67 06,681 Uniroyal, Inc.) G. A. White et al. "Pesticide Biochemistry and Physiology" 5, 380–395 (1975) and M. Shell et al. "Phytopathology" 60, 1164–1169 (1970).

However, the compounds mentioned in these literatures are insufficient in their activities and are not necessarily satisfactory. Thus, chemicals without these defects have been demanded.

As a result of the inventors' extensive research on compounds having fungicidal activity, it has been found that heterocyclic derivatives represented by the following formula (I) have superior fungicidal activity less in said defects. The present invention is based on this finding.

That is, the present invention provides a heterocyclic derivative (referred to as "present compound" hereinfter) represented by the formula:

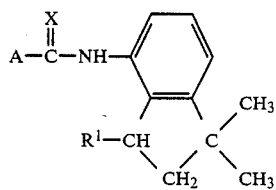
(I)

(wherein $R^1$ represents a hydrogen atom or a methyl group, A represents

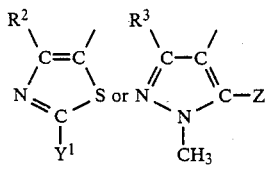

wherein $R^2$ represents a methyl group, an ethyl group or trifluoromethyl group, $Y^1$ represents an amino group, a methyl group or a chlorine atom, $R^3$ represents a methyl group or a trifluoromethyl group and Z represents a hydrogen atom, a halogen atom or a methyl group and when A is

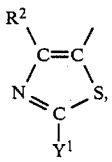

X represents an oxygen atom or a sulfur atom and when A is

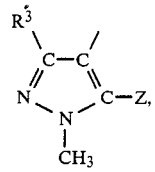

X represents a sulfur atom), a method for preparing the same and a fungicide containing the derivative as an active ingredient.

The present compound has preventive, curative and systemic controlling effects on various plant microbes, especially on plant diseases caused by microbes belonging to Basidiomycetes and has substantially no adverse effects on environment.

The following are plant diseases on which the present compound has an excellent controlling effect;

Rhizoctonia solani and *Rhizoctonia oryzae, R. solani* III B on rice plant; *Puccinia striformis, P. graminis, P. recondita, P. hordei, Typhula incarnata, T. ishikariensis, Ustilago tritici* and *U. nuda* on wheat and barley; *Rhizoctonia solani* and *Corticium rolfsii* on various crops; *Rhizoctonia solani* on potato and beet; *Gymnosporangium haraeanum* on pear; *Venturia inaequaris* on apple; *Rhizoctonia solani, Corticium rolfsii, Uromyces trifolii* and *Typhula incarnata, T. ishikariensis* on pasture and lawn.

Method for preparing the present compound will be explained in detail below.

[Method (a)]

Among the present compounds, a heterocyclic derivative represented by the formula:

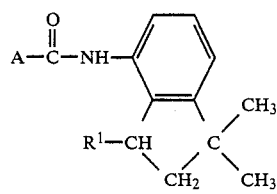
(II)

(wherein A and $R^1$ have the same meanings as defined above) is prepared by allowing a heterocyclic carboxylic acid represented by the formula:

A—COOH (III)

(wherein A has the same meaning as defined above) or its reactive derivative to react with an aminoindan derivative represented by the formula:

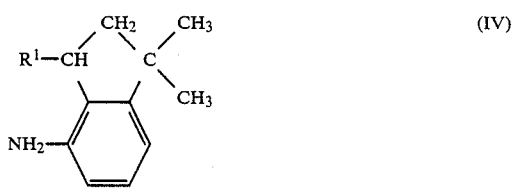
(IV)

(wherein $R^1$ has the same meaning as defined above).

In the above reaction, solvents are not essential, but usually the reaction is effected in the presence of solvents.

The solvents are, for example hydrocarbons such as benzene, toluene and xylene, halogenated hydrocarbons such as chlorobenzene, methylene chloride, chloroform and carbon tetrachloride, ethers such as diisopropyl ether, tetrahydrofuran and dioxane, ketones such as acetone, and methyl ethyl ketone, esters such as ethyl acetate, nitriles such as acetonitrile, dimethylsulfoxide, dimethylformamide, water, etc.

Amount of the starting compounds used in said reaction is 0.4–1.5 equivalent, preferably 0.5–1.1 equivalent of the heterocyclic carboxylic acid or its reactive derivative represented by the formula (III) per one equivalent of the aminoindan derivative represented by the formula (IV).

Said reaction is carried out at optional temperature from the freezing point to the boiling point of solvents, preferably from 0° C. to boiling point of solvents.

The heterocyclic carboxylic acid represented by the formula (III) or its reactive derivative includes the corresponding carboxylic acids, acid anhydrides, acid chlorides, acid bromides, carboxylic esters, etc.

Said reaction is effected in the presence of suitable reaction assistants depending on the heterocyclic carboxylic acids represented by the formula (III) or reactive derivatives thereof. As the reaction assistants, there may be used dicyclohexylcarbodiimide, phosphorus pentachloride, etc. when carboxylic acid is used, and sodium methoxide, sodium ethoxide, etc. when carboxylic ester is used. Furthermore, when acid halide or acid anhydride is used, sodium hydroxide, potassium hydroxide, triethylamine, N-methylmorpholine, etc. may be used as the assistant.

Generally, the reaction assistants are used in an amount of from catalytic amount to 2 equivalents, preferably 0.95–1.1 equivalents.

After completion of the reaction, the reaction mixture is subjected to filtration, washing with water, etc., followed by removal of solvent by distillation. If necessary, the residue is subjected to recrystallization, etc. to obtain the objective compound.

[Method (b)]

Among the present compounds, a thiazolecarboxylic acid derivative represented by the formula:

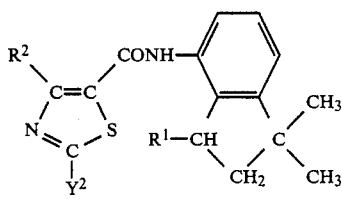

(V)

(wherein $R^1$ and $R^2$ have the same meanings as defined above and $Y^2$ represents an amino group or a methyl group) is produced by allowing an aminoindan derivative represented by the formula:

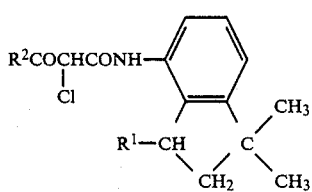

(VI)

(wherein $R^1$ and $R^2$ have the same meanings as defined above) to react with a thioamide derivative represented by the formula:

(VII)

(wherein $Y^2$ has the same meaning as defined above).

Reaction solvent is not essential for said reaction, but usually the reaction is effected on the presence of a solvent. Examples of the solvent are hydrocarbons such as benzene, toluene and xylene, halogenated hydrocarbons such as chlorobenzene, ethers such as diisopropyl ether, tetrahydrofuran and dioxane, esters such as ethyl acetate, alcohols such as methanol and ethanol, dimethylsulfoxide, dimethylformamide, water, etc.

Amount of the starting compounds has no special limitation, but usually is 0.5–10 equivalents, preferably 1–3 equivalents of the thioamide derivative represented by the formula (VII) per one equivalent of the aminoindan derivative represented by the formula (VI).

The above reaction is effected at optional temperature of from the freezing point to the boiling point of the solvent, preferably from 0° C. to the boiling point of the solvent.

If necessary, a base as reaction assistant may also be used. Examples of the base are amines such as aqueous ammonia, triethylamine and N-methylmorpholine and inorganic bases such as potassium carbonate and sodium carbonate.

After completion of reaction, the reaction mixture is subjected to filtration, washing with water, etc., followed by removal of solvent by distillation and, if necessary, the residue is further subjected to recrystallization, chromatography, etc. to obtain the objective compound.

[Method (c)]

Among the present compounds, heterocyclic derivative represented by the formula:

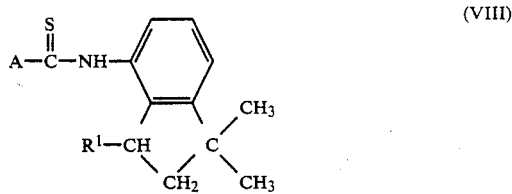

(VIII)

(wherein A and $R^1$ have the same meanings as defined above) is produced by allowing a heterocyclic carboxylic acid derivative represented by the formula (II) to react with a thionating agent.

As examples of the thionating agent, mention may be made of phosphorus pentasulfide, 2,4-bis(methylthio)-1,3,2,4-dithiadiphosphetan-2,4-disulfide, 2,4-bis(p-methoxyphenyl)-1,3,2,4-dithiadiphosphetan-2,4-disulfide, etc.

Reaction solvent is not essential for this reaction, but usually the reaction is effected in the presence of a solvent.

Amount of the starting compounds used for the reaction has no special limitation, but usually is 0.5–20 equivalents, preferably 1–10 equivalents of the thionating agent per one equivalent of the heterocyclic carboxylic acid derivative represented by the formula (II).

This reaction is carried out at optional temperature of from the freezing point to the boiling point of the solvent, preferably from 0° C. to the boiling point of the solvent.

After completion of the reaction, the reaction mixture is subjected to concentration or extraction and washing with water and then, if necessary, to recrystallization, etc. to obtain the objective heterocyclic derivative represented by the formula (VIII).

A pyrazole carboxamide compound represented by the formula:

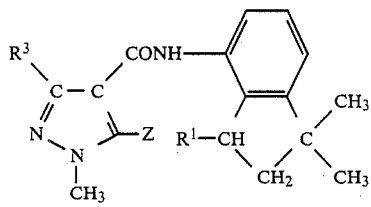

(wherein $R^1$, $R^3$ and Z have the same meanings as defined above) which is a starting material for preparation of the present compound (wherein A represents

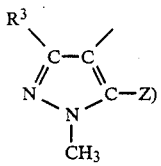

is produced, for example, by the following methods.

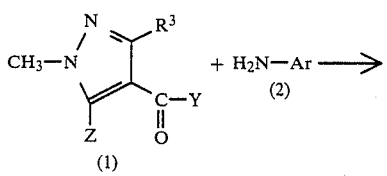

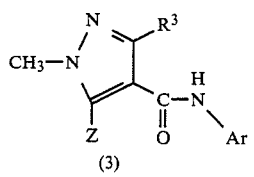

wherein $R^3$ and Z are as defined above, Y represents a halogen atom and Ar represents a group having the formula:

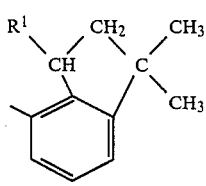

(wherein $R^1$ is as defined above).

That is, a carboxylic acid halide represented by the formula (1), e.g., carboxylic acid chloride, carboxylic acid bromide and carboxylic acid fluoride, is treated with a 4-aminoindan derivative represented by the formula (2) to obtain the pyrazole carboxamide compound represented by the formula (3).

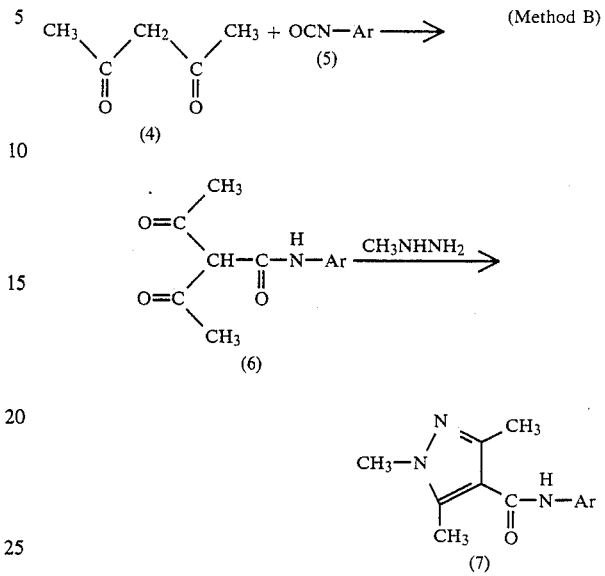

wherein Ar is as defined above.

That is, an acetyl acetone represented by the formula (4) is treated with an isocyanate represented by the formula (5) to obtain a carbamoyl diketone represented by the formula (6), which is then allowed to react with methylhydrazine to obtain the pyrazolecarboxamide compound represented by the formula (7).

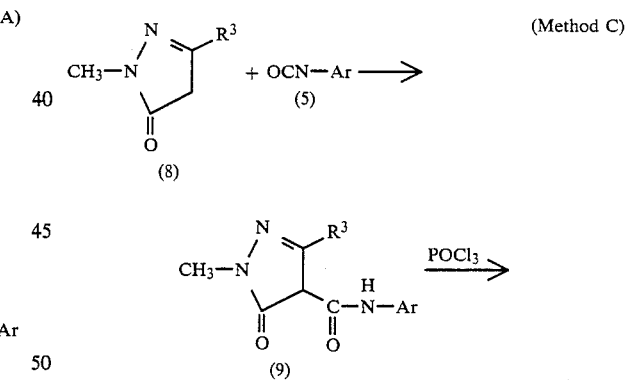

wherein $R^3$ and Ar are as defined above.

That is, a pyrazoline-5-one represented by the formula (8) is allowed to react with an isocyanate represented by the formula (5) to obtain a 4-carbamoyl-pyrazoline-5-one represented by the formula (9), which is then allowed to react with phosphorus oxychloride to obtain a chlorine-substituted pyrazolecarboxamide compound represented by the formula (10).

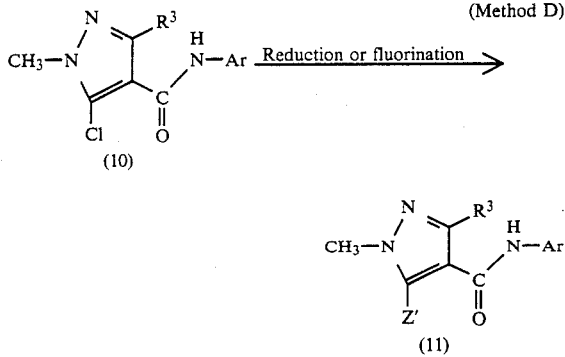

(Method D)

wherein R³ and Ar are as defined above and Z' represents a hydrogen or fluorine atom.

That is, the chlorine-substituted pyrazolecarboxamide compound of formula (10) obtained by (method C) is subjected to reduction reaction to replace a chlorine atom with a hydrogen atom or is subjected to chlorine-/fluorine replacing reaction with a fluorinating agent to obtain the pyrazolecarboxamide compound represented by the formula (11).

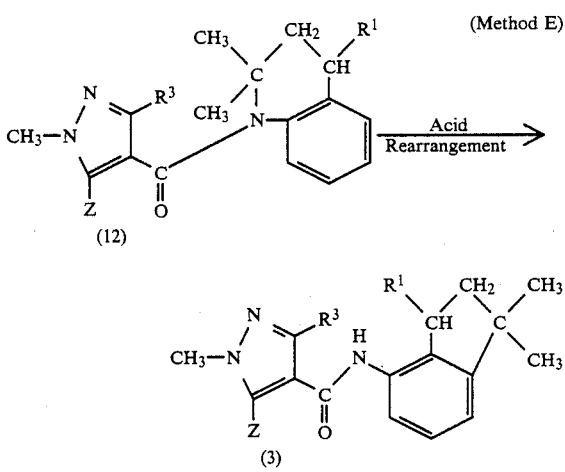

(Method E)

wherein R¹, R³ and Z are as defined above.

That is, a tetrahydroquinoline represented by the formula (12) is subjected to rearrangement in the presence of an acid catalyst to obtain the pyrazolecarboxamide derivative represented by the formula (3).

Examples of the present compounds (wherein A represents

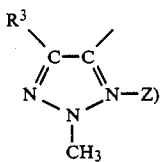

are as follows:
1,3-Dimethyl-N-(1,1-dimethyl-4-indanyl)pyrazole-4-carbothioamide
1,3,5-Trimethyl-N-(1,1-dimethyl-4-indanyl)pyrazole-4-carbothioamide
1,3-Dimethyl-5-fluoro-N-(1,1-dimethyl-4-indanyl)-pyrazole-4-carbothioamide
1,3-Dimethyl-5-chloro-N-(1,1-dimethyl-4-indanyl)-pyrazole-4-carbothioamide
1,3-Dimethyl-5-bromo-N-(1,1-dimethyl-4-indanyl)-pyrazole-4-carbothioamide
1,3-Dimethyl-5-iodo-N-(1,1-dimethyl-4-indanyl)-pyrazole-4-carbothioamide
1,3-Dimethyl-N-(1,1,3-trimethyl-4-indanyl)pyrazole-4-carbothioamide
1,3,5-Trimethyl-N-(1,1,3-trimethyl-4-indanyl)Pyrazole-4-carbothioamide
1,3-Dimethyl-5-fluoro-N-(1,1,3-trimethyl-4-indanyl)-pyrazole-4-carbothioamide
1,3-Dimethyl-5-chloro-N-(1,1,3-trimethyl-4-indanyl)-pyrazole-4-carbothioamide
1,3-Dimethyl-5-bromo-N-(1,1,3-trimethyl-4-indanyl)-pyrazole-4-carbothioamide
1,3-Dimethyl-5-indo-N-(1,1,3-trimethyl-4-indanyl)-pyrazole-4-carbothioamide
1-Methyl-3-trifluoromethyl-N-(1,1,3-trimethyl-4-indanyl)pyrazole-4-carbothioamide
1,5-Dimethyl-3-trifluoromethyl-N-(1,1,3-trimethyl-4-indanyl)pyrazole-4-carbothioamide
1-Methyl-3-trifluoromethyl-5-chloro-N-(1,1,3-trimethyl-4-indanyl)pyrazole-4-carbothioamide
1-Methyl-3-trifluoromethyl-5-fluoro-N-(1,1,3-trimethyl-4-indanyl)pyrazole-4-carbothioamide
1-Methyl-3-trifluoromethyl-5-bromo-N-(1,1,3-trimethyl-4-indanyl)pyrazole-4-carbothioamide
1-Methyl-3-trifluoromethyl-5-iodo-N-(1,1,3-trimethyl-4-indanyl)pyrazole-4-carbothioamide
1-Methyl-3-trifluoromethyl-N-(1,1-dimethyl-4-indanyl)pyrazole-4-carbothioamide
1,5-Dimethyl-3-trifluoromethyl-N-(1,1-dimethyl-4-indanyl)pyrazole-4-carbothioamide
1-Methyl-3-trifluoromethyl-5-fluoro-N-(1,1-dimethyl-4-indanyl)pyrazole-4-carbothioamide
1-Methyl-3-trifluoromethyl-5-chloro-N-(1,1-dimethyl-4-indanyl)pyrazole-4-carbothioamide
1-Methyl-3-trifluoromethyl-5-bromo-N-(1,1-dimethyl-4-indanyl)pyrazole-4-carbothioamide
1-Methyl-3-trifluoromethyl-5-iodo-N-(1,1-dimethyl-4-indanyl)pyrazole-4-carbothioamide When the present compound is used as an active ingredient of fungicides, it may be used without adding any other components, but generally, it is formulated into emulsifiable concentrates, wettable powders, suspension formulations, granules, dusts, liquids and the like by mixing with a solid or liquid carrier, a surface active agent and other auxiliaries for formulation.

The content of the present compound as an active ingredient in these formulations is 0.1 to 99.9%, preferably 0.2 to 80% by weight.

The solid carriers include, for example, fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide and the like. The liquid carrier includes for example aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cotton seed oil and the like, dimethyl sulfoxide, acetonitrile, water and the like.

The surface active agents used for emulsification, dispersion, wetting, etc. include, for example, anionic surface active agents such as salts of alkyl sulfate, alkyl (aryl) sulfonates, dialkyl-sulfosuccinates, salts of polyoxyethylene alkylaryl ether phosphoric acid esters, naphthalenesulfonic acid/formalin condensates, etc. and nonionic surface active gents such as polyoxyethylene alkyl ether, polyoxyethylene polyoxypropylene block copolymers, sorbitan fatty acid esters, polyoxyethylene sorbitan fatty acid esters, etc. The auxiliaries for formulation include, for example, lignosulfonates, alginates, polyvinyl alcohol, gum arabic, CMC (carboxymethyl cellulose), PAP (acid isopropyl phosphate), etc.

These formulations as such or diluted with, for example, water are applied to soil or directly to plants. In more detail, they are used in various forms, e.g., spraying or dusting on plants or spraying, dusting or granule-sprinkling onto soil surface or if necessary subsequent further soil incorporation. Furthermore, when they are used as seed treating agents, seeds are covered therewith or dipped therein.

Fungicidal effects can be expected to be further increased by using them in admixture with other fungicides. Furthermore, these formulations may also be used in admixture with insecticides, acaricides, nematocides, herbicides, plant growth regulating agent, fertilizers, soil improvers and the like.

The present compounds can be used as an active ingredient of fungicides to be used for paddy field, plowland, orchard, pasture, turf and the like.

When the present compound is used as an active ingredient of fungicide, its dosage is generally 0.5 to 100 g, preferably 1 to 50 g per are, although it depends on weather conditions, form of formulations, time, method and place of application, diseases to be controlled, crops to be treated, etc. When the emulsifiable concentrate, wettable powder, suspension formulation, liquid formulation, etc. are diluted with water for use, the concentration is 0.001% to 1%, preferably 0.005% to 0.5%. Granule and dust are used as they are without dilution.

The present invention will be explained in more detail by the following synthesis examples, reference examples, formulation examples and test examples.

SYNTHESIS EXAMPLE 1

[Synthesis of compound (5) by method (a)]

To a solution of 0.82 g (5.07 mmol) of 1,1-dimethyl-4-aminoindan and 0.48 g (6.08 mmol) of pyridine in 10 ml of tetrahydrofuran was added dropwise with stirring below 5° C. under ice cooling, a solution of 0.99 g (5.07 mmol) of 2-chloro-4-methylthiazole-5-carboxylic acid chloride in 3 ml of tetrahydrofuran, followed by stirring at room temperature overnight. The reaction mixture was poured into water and extracted with ethyl acetate. The organic layer was washed with 5% hydrochloric acid and then water and was dried over anhydrous sodium sulfate. The solvent was distilled off to obtain crystals, which was washed with n-hexane and dried to obtain 1.51 g of N-(1,1-dimethyl-4-indanyl)-2-chloro-4-methylthiazole-5-carboxamide (yeild 93%).

SYNTHESIS EXAMPLE 2

[Synthesis of compound (6) by method (a)]

252 mg (1.42 mmol) of 2-chloro-4-methylthiazole-5-carboxylic acid and 442 mg (1.42 mmol) of 1-(3-dimethylaminopropyl)-3-ethylcarbodiimidomethiodide were dissolved in 10 ml of methylene chloride and stirred at room temperature for 1 hour. Then, to the solution was added 249 mg (1.42 mmol) of 1,1,3-trimethyl-4-aminoindan and reaction was effected for 6 hours under reflux. The reaction mixture was poured into water and extracted with methylene chloride. The organic layer was concentrated and thereafter was purified by column chromatography (eluent; n-hexane:ethyl acetate=50:50 V/V) to obtain 204 mg of N-(1,1,3-trimethyl-4-indanyl)-2-chloro-4-methylthiazole-5-carboxamide (yield 43%).

SYNTHESIS EXAMPLE 3

[Synthesis of compound (4) by method (b)]

1.00 g (4.08 mmol) of N-(1,1-dimethyl-4-indanyl)acetoacetamide and 0.62 g (8.16 mmol) of thiourea were dissolved in 10 ml of benzene and to this solution was added dropwise a solution of 0.55 g (4.08 mmol) of sulfuryl chloride in 5 ml of benzene at room temperature. After reacting for 2 hours at this temperature, the reaction mixture was refluxed for 1 hour, and left overnight. Then, the resulting solution was concentrated and dissolved in hot water and thereafter neutralyzed with 28% aqueous ammonia to give a precipitate. This precipitate was filtered, washed with water and dried to obtain 1.00 g of N-(1,1-dimethyl-4-indanyl)-2-amino-4-methylthiazole-5-carboxamide (yield 81%).

SYNTHESIS EXAMPLE 4

[Synthesis of compound (3) by method (b)]

1.14 g (4.08 mmol) of N-(1,1-dimethyl-4-indanyl)-2-chloroacetoacetamide and 0.30 g (4.08 mmol) of thioacetamide were dissolved in 10 ml of tetrahydrofuran and was refluxed for 3 hours. To the reaction mixture was added 0.56 g (4.08 mmol) of anhydrous potassium carbonate and reaction was effected for 4 hours under reflux. The resulting solution was added to water and extracted with ethyl acetate. The organic layer was concentrated and then purified by column chromatography (eluent; n-hexane:ethyl acetate=50:50 V/V) to obtain 0.52 g of N-(1,1-dimethyl-4-indanyl)-2,4-dimethylthiazole-5-carboxamide (yield 43%).

SYNTHESIS EXAMPLE 5

[Synthesis of compound (12) by method (c)]

0.20 g of N-(1,1,3-trimethyl-4-indanyl)-2-methyl-4-trifluoromethylthiazole-5-carboxamide and 0.18 g of 2,4-bis(methylthio)-1,3,2,4-dithiadiphosphetan-2,4-disulfide were dissolved in 5 ml of tetrahydrofuran and reaction was effected for 10 hours under reflux. The reaction mixture was concentrated and the residue was chromatographed on silica gel (eluent; n-hexane:chloroform:tetrahydrofuran=6:2:1) to obtain 0.14 g of N-(1,1,3-trimethyl-4-indanyl)-2-methyl-4-trifluoromethylthiazole-5-carbothioamide (yield 65%).

SYNTHESIS EXAMPLE 6

[Synthesis of compound (18) by method (c)]

To a solution of 1.0 g of 1,3,5-trimethyl-N-(1,1,3-trimethyl-4-indanyl)pyrazolecarboxamide in 20 ml of dimethoxyethane was added 914 mg of 2,4-bis(methylthio)-1,3,2,4-dithiadiphosphetan-2,4-disulfide with stirring, followed by stirring for 10 hours at room temperature and for 1 hour at 50° C. After cooling, the reaction mixture was chromatographed on silica gel to obtain 0.89 g of 1,3,5-trimethyl-N-(1,1,3-trimethylindane-4-yl)pyrazole carbothioamide (yield 85%).

SYNTHESIS EXAMPLE 7

[Synthesis of compound (18) by method (c)]

1.1 g of 1,3,5-trimethyl-N-(1,1,3-trimethyl-4-indanyl)-pyrazole-4-carboxamide, 0.79 g of phosphorus pentasulfide and 15 ml of hexamethylphosphoramide (HMPA) were stirred at 100° C. for 8 hours. After cooling, the reaction mixture was poured into ice water and extracted with ether. The extracts ether layer were dried over anhydrous magnesium sulfate and then the solvent was distilled off. The residue was chromatographed on silica gel to obtain 0.75 g of 1,3,5-trimethyl-N-(1,1,3-trimethylindane-4-yl)pyrazole-4-carbothioamide (yield 65%).

Some of representative compounds of the present invention which can be produced by these methods are shown in Table 1.

TABLE 1

Compounds represented by the formula:

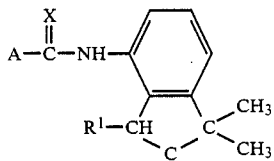

| Compound No. | A | $R^1$ | X | Properties |
|---|---|---|---|---|
| (1) | 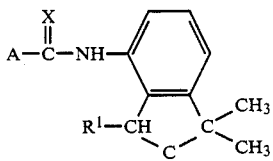 | $CH_3$ | O | mp 260–261° C. |
| (2) | 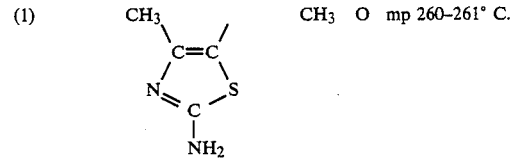 | $CH_3$ | O | Glassy |
| (3) | 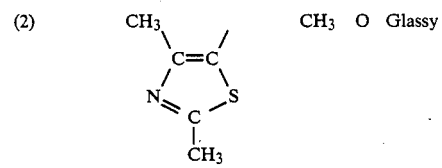 | H | O | mp 106.1° C. |
| (4) | 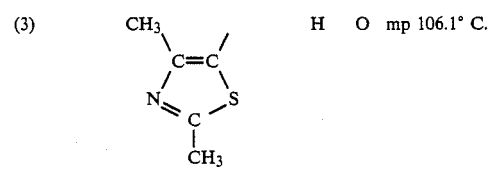 | H | O | mp 199–203° C. |
| (5) | 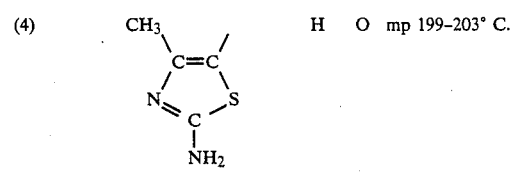 | H | O | mp 154.8° C. |
| (6) | 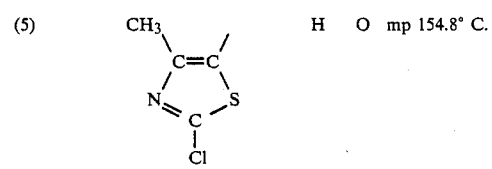 | $CH_3$ | O | mp 103.2° C. |
| (7) | 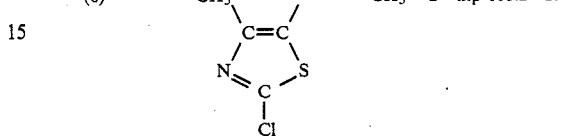 | $CH_3$ | O | mp 102.8° C. |
| (8) | 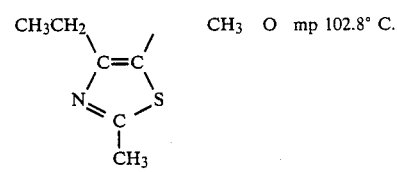 | $CH_3$ | S | Glassy |
| (9) | 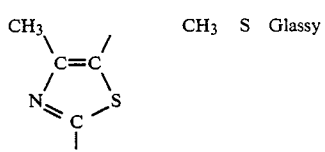 | $CH_3$ | S | Glassy |
| (10) | 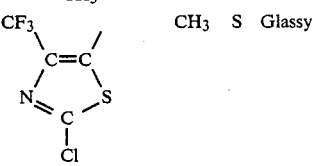 | $CH_3$ | O | mp 153.0° C. |
| (11) | 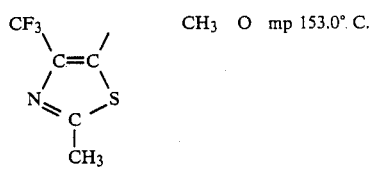 | H | O | mp 130–132° C. |
| (12) | 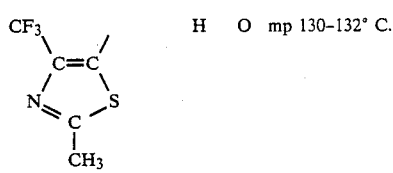 | $CH_3$ | S | mp 172–175° C. |
| (13) | 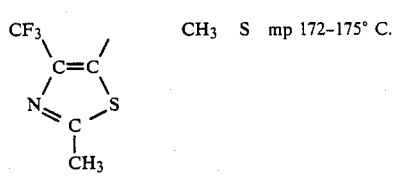 | H | S | mp 177.0° C. |

TABLE 1-continued

Compounds represented by the formula:

A—C(=X)—NH—[phenyl with R¹—CH— and —C(CH₃)₂— forming ring via C]

| Compound No. | A | R¹ | X | Properties |
|---|---|---|---|---|
| (14) | 1,3-dimethyl-pyrazol-4-yl (CH₃ at C3, CH₃ at N, H at C5) | H | S | mp 169.5° C. |
| (15) | 3-methyl-5-fluoro-1-methylpyrazol-4-yl | H | S | mp 119.9° C. |
| (16) | 3-methyl-5-chloro-1-methylpyrazol-4-yl | H | S | mp 119.5° C. |
| (17) | 1,3-dimethylpyrazol-4-yl | CH₃ | S | mp 208.0° C. |
| (18) | 1,3,5-trimethylpyrazol-4-yl | CH₃ | S | mp 199.2° C. |
| (19) | 3-methyl-5-fluoro-1-methylpyrazol-4-yl | CH₃ | S | mp 186.4° C. |
| (20) | 3-methyl-5-chloro-1-methylpyrazol-4-yl | CH₃ | S | mp 164.9° C. |
| (21) | 3-trifluoromethyl-1-methylpyrazol-4-yl | CH₃ | S | mp 175.3° C. |
| (22) | 3-trifluoromethyl-1-methylpyrazol-4-yl | H | S | mp 141.3° C. |
| (23) | 3-trifluoromethyl-5-chloro-1-methylpyrazol-4-yl | CH₃ | S | mp 163.9° C. |

Preparation of 2-methyl-4-trifluoromethylthiazole-5-carboxylic acid derivative among the starting compounds used for the synthesis of the present compounds will be explained in detail below.

REFERENCE EXAMPLE 1

Synthesis of ethyl 2-methyl-4-trifluoromethylthiazole-5-carboxylate 6.00 g of ethyl 2-chloro-4,4,4-trifluoroacetoacetate and 2.06 g of thioacetamide were dissolved in 30 ml of acetic acid and the mixture was refluxed for 6 hours with stirring. The resulting solution was neutralized with aqueous sodium bicarbonate solution, then extracted with ethyl acetate and the organic layer was concentrated. The residue was chromatographed on silica gel (eluent; n-hexane:chloroform:tetrahydrofuran=6:2:1 V/V) to obtain 3.7 g of ethyl 2-methyl-4-trifluoromethylthiazole-5-carboxylate (yield 56%).

PMR (CDCl₃) δ 4.33 (2H, q, J=7.0 Hz), 2.72(3H, s), 1.36(3H, t, J=7.0 Hz),

F-NMR(CDCl₃/CF₃COOH) δ+17.0(3F, s)

REFERENCE EXAMPLE 2

Synthesis of 2-methyl-4-trifluoromethylthiazole-5-carboxylic acid 1.3 g of ethyl 2-methyl-4-trifluoromethylthiazole-5-carboxylate and 0.4 g of potassium hydroxide were dissolved in a mixture of 5 ml each of water and ethanol and reaction was effected at room temperature overnight. After the reaction, the reaction mixture was concentrated and acidified with dilute hydrochloric acid and extracted with ethyl acetate. The extract was concentrated to obtain 0.89 g of 2-methyl-4-trifluoromethylthiazole-5-carboxylic acid.

REFERENCE EXAMPLE 3

Synthesis of 2-methyl-4-trifluoromethylthiazole-5-carbonyl chloride 0.50 g of 2-methyl-4-trifluoromethylthiazole-5-carboxylic acid was added to 5 ml of thionyl chloride and reaction was carried out for 2 hours under reflux. After the reaction, the reaction mixture was concentrated to obtain 0.54 g of 2-methyl-4-trifluoromethylthiazole-5-carbonyl chloride.

The following are formulation examples where the present compounds used are indicated by the numbers given in Table 1 and parts or % are by weight.

FORMULATION EXAMPLE 1

Fifty parts of each of the present compounds (1)–(23), 3 parts of calcium lignosulfonate, 2 parts of sodium lauryl sulfate and 45 parts of synthetic hydrated silicon dioxide are thoroughly pulverized and mixed to obtain a wettable powder containing an active ingredient concentration of 50%.

FORMULATION EXAMPLE 2

Ten parts of each of the present compounds (1)–(23), 14 parts of polyoxyethylenestyrylphenyl ether, 6 parts of calcium dodecylbenzenesulfonate and 70 parts of xylene are thoroughly mixed to obtain an emulsifiable concentrate containing an active ingredient concentration of 10%.

FORMULATION EXAMPLE 3

Two parts of each of the present compounds (1)–(23), 1 part of synthetic hydrated silicon dioxide, 2 parts of calcium lignosulfonate, 30 parts of bentonite, and 65 parts of kaolin clay are thoroughly pulverized and mixed, well kneaded with water, then granulated and dried to obtain a granule containing an active ingredient concentration of 2%.

FORMULATION EXAMPLE 4

Twentyfive parts of each of the present compounds (1)–(23), 3 parts of polyoxyethylenesorbitan monooleate, 3 parts of CMC and 69 parts of water are mixed and wet-pulverized to particle size of not more than 5 microns to obtain a suspension formulation containing an active ingredient concentration of 25%.

FORMULATION EXAMPLE 5

Two parts of each of the present compounds (1)–(23), 88 parts of kaolin clay and 10 parts of talc are thoroughly pulverized and mixed to obtain a dust containing an active ingredient concentration of 2%.

FORMULATION EXAMPLE 6

Ten parts of each of the present compounds (1)–(23), 1 part of polyoxyethylenestyrylphenyl ether and 89 parts of water are mixed to obtain a liquid containing an active ingredient concentration of 10%.

The effect of the present compounds as an active ingredient of fungicides will be shown by the following test examples. The present compounds used are indicated by the compound number given in Table 1 and the compounds used for comparison are indicated by the compounds given in Table 2.

TABLE 2

| Compounds | Chemical formula | Note |
|---|---|---|
| A | (structure with CH₃, OCH(CH₃)₂, CNH, O) | Commercially available fungicide (mepronil) |
| B | CCl₃—CH—NHCHO / N / (piperazine ring) / N / CCl₃—CH—NHCHO | Commercially available fungicide (triforine) |
| C | (thiazole structure with CH₃, C=C, CONH-phenyl, N, S, C, CH₃) | Compound mentioned in Phytopathology 60, 1164–1169 (1970) |
| D | (structure with S, O, CNH-phenyl, O, CH₃) | Commercially available fungicide (carboxin) |
| E | (pyrazole structure with CH₃, C—C, CONH-phenyl, N, N, C—CH₃, CH₃) | Compound mentioned in German Patent 2701091 |

The controlling effect is determined by observing with the naked eye the condition of disease of test plants on examination, namely, the degree of fungus colony and infected area of leaf and stem and grading the condition of diseases into the following six indisease 0, 1, 2, 3, 4 and 5:

5 ... No infected area and fungus colony are noticed.
4 ... Infected area and fungus colony are noticed in about 10% of leaf and stem.
3 ... Infected area and fungus colony are noticed in about 30% of leaf and stem.
2 ... Infected area and fungus colony are noticed in about 50% of leaf and stem.
1 ... Infected area and fungus colony are noticed in about 70% of leaf and stem.
0 ... Infected area and fungus colony are noticed in more than about 70% and no difference is noticed from the condition of disease when no compound is used.

The above grading is applied to all of the following test examples.

TEST EXAMPLE 1

Test for preventive controlling effect on sheath blight (*Rhizoctonia solani*) of rice.

Sandy loam was filled in a plastic pot and rice (var.: kinki No. 33) was sowed and cultivated in a greenhouse for 60 days to grow to seedlings in the 6–7 leaf stages. The test compounds were formulated into emulsifiable concentrates in accordance with the Formulation Example 2 and they were diluted with water to a given concentration. These were foliar-sprayed onto the seedlings to allow them to thoroughly deposit on the leaf surface. After 4 hours from the spraying, the seedlings were inoculated by putting agar piece containing *Rhizoctonia solani*. After inoculation, the seedlings were grown at 28° C. for 4 days under highly humid condition and the controlling effects were observed. The results are shown in Table 3.

TABLE 3

| Test compounds | Concentration of active ingredient (ppm) | Controlling effect |
|---|---|---|
| (1) | 50 | 5 |
|  | 25 | 5 |
|  | 12.5 | 5 |
| (2) | 50 | 5 |
|  | 25 | 5 |
|  | 12.5 | 5 |
| (3) | 50 | 5 |
|  | 25 | 5 |
|  | 12.5 | 5 |
| (4) | 50 | 5 |
|  | 25 | 5 |
|  | 12.5 | 5 |
| (5) | 50 | 5 |
|  | 25 | 5 |
|  | 12.5 | 5 |
| (6) | 50 | 5 |
|  | 25 | 5 |
|  | 12.5 | 5 |
| (7) | 50 | 5 |
|  | 25 | 5 |
|  | 12.5 | 5 |
| (8) | 50 | 5 |
|  | 25 | 5 |
|  | 12.5 | 5 |
| (10) | 50 | 5 |
|  | 25 | 5 |
|  | 12.5 | 5 |
| (11) | 50 | 5 |
|  | 25 | 5 |
|  | 12.5 | 5 |
| (12) | 50 | 5 |
|  | 25 | 5 |
|  | 12.5 | 5 |
| (13) | 50 | 5 |
|  | 25 | 5 |
|  | 12.5 | 5 |
| (14) | 50 | 5 |
|  | 25 | 5 |
|  | 12.5 | 5 |
| (15) | 50 | 5 |
|  | 25 | 5 |
|  | 12.5 | 5 |
| (16) | 50 | 5 |
|  | 25 | 5 |
|  | 12.5 | 5 |
| (17) | 50 | 5 |
|  | 25 | 5 |
|  | 12.5 | 5 |
| (18) | 50 | 5 |
|  | 25 | 5 |
|  | 12.5 | 5 |
| (19) | 50 | 5 |
|  | 25 | 5 |
|  | 12.5 | 5 |
| (20) | 50 | 5 |
|  | 25 | 5 |
|  | 12.5 | 5 |
| (21) | 50 | 5 |
|  | 25 | 5 |
|  | 12.5 | 5 |
| (22) | 50 | 5 |
|  | 25 | 5 |
|  | 12.5 | 5 |
| (23) | 50 | 5 |
|  | 25 | 5 |
|  | 12.5 | 5 |
| A | 50 | 3 |
|  | 25 | 0 |
| C | 50 | 2 |
|  | 25 | 0 |

TABLE 3-continued

| Test compounds | Concentration of active ingredient (ppm) | Controlling effect |
|---|---|---|
| E | 50 | 2 |
|  | 25 | 1 |

TEST EXAMPLE 2

Test for systemic controlling effect on sheath blight (*Rhizoctonia solani*) of rice.

Sandy loam was filled in a 130 ml plastic pot and rice (var.: Kinki No. 33) was sowed and cultivated in a greenhouse for 8 weeks to grow to seedlings in the 6–7 leaf stages. The test compounds formulated in to wettable powders in accordance with Formulation Example 1 and they were diluted with water and drenched in a given amount to the soil. After drench, the seedlings were grown in a greenhouse for 7 days and inoculated by putting agar piece containing *Rhizoctonia solani*. After inoculation, the seedlings were grown at 28° C. for 4 days under a highly humid condition and the controlling effect was observed. The results are shown in Table 4.

TABLE 4

| Test compounds | Dosage of active ingredient (g/10a) | Controlling effect |
|---|---|---|
| (2) | 100 | 5 |
| (3) | 100 | 5 |
| (10) | 100 | 5 |
| (18) | 100 | 5 |
| A | 200 | 2 |

TEST EXAMPLE 3

Test for controlling effect on southern blight (*corticium rolfsii*) of kidney bean.

Sandy loam well mixed with *Corticium rolfsii* which was previously cultured in bran medium was filled in a 250 ml plastic pot and kidney bean (var.: Taishokintoki) was sowed. The test compounds were formulated into wettable powders in accordance with Formulation Example 1 and diluted with water. A given amount of the test compound was drenched into the soil. After the drench, cultivation was made for 3 weeks in a greenhouse and controlling effect was examined by observing the degree of disease of the stem in the vicinity of the soil surface. The results are shown in Table 5.

TABLE 5

| Test compounds | Dosage of active ingredient (g/10a) | Controlling effect |
|---|---|---|
| (1) | 200 | 5 |
| (2) | 200 | 5 |
| (3) | 200 | 5 |
| (4) | 200 | 5 |
| (5) | 200 | 5 |
| (6) | 200 | 5 |
| (7) | 200 | 5 |
| (8) | 200 | 5 |
| (9) | 200 | 5 |
| (10) | 200 | 5 |
| (18) | 200 | 5 |
| (19) | 200 | 5 |
| A | 500 | 3 |

TEST EXAMPLE 4.

Test for controlling effect on Loose smut (*Ustilago tritici*) of wheat in seed treatment.

The test compounds were formulated into wettable powders in accordance with Formulation Example 1 and diluted with water to a given concentration. In these solutions were dipped wheat seeds (var.: Norin No. 73) inoculated with *Ustilago tritici* for 24 hours. Then, the seeds were sowed in field and cultivated. Controlling effect was determined by the condition of disease of the heads. The results are shown in Table 6.

TABLE 6

| Test compounds | Dosage of active ingredient (g/100 Kg of seeds) | Controlling effect |
|---|---|---|
| (2) | 60 | 5 |
| (10) | 60 | 5 |
| D | 60 | 5 |

TEST EXAMPLE 5

Test for curative controlling effect on brown rust (*Puccinia recondita*) of wheat.

Sandy loam was filled in a plastic pot and wheat (var.: Norin No. 73) was sowed and grown in a greenhouse for 10 days to seedlings of the 2–3 leaf stages, which were inoculated with a spore of *Puccinia recondita*. After inoculation, the seedlings were grown at 23° C. for one day under a highly humid condition and onto these seedlings was foliar-sprayed the test compound formulated into emulsifiable concentrate in accordance with Formulation Example 2 and diluted with water to a given concentration, so that the compound was thoroughly deposited on the leaf surface. After spraying, the seedlings were cultivated at 23° C. for 7 days under illumination and the controlling effect was observed. The results are shown in Table 7.

TABLE 7

| Test compounds | Concentration of active ingredient (ppm) | Controlling effect |
|---|---|---|
| (1) | 100 | 5 |
|  | 50 | 5 |
|  | 25 | 5 |
| (2) | 100 | 5 |
|  | 50 | 5 |
|  | 25 | 5 |
| (3) | 100 | 5 |
|  | 50 | 5 |
|  | 25 | 5 |
| (4) | 100 | 5 |
|  | 50 | 5 |
|  | 25 | 5 |
| (18) | 100 | 5 |
|  | 50 | 5 |
|  | 25 | 5 |
| (19) | 100 | 5 |
|  | 50 | 5 |
|  | 25 | 5 |
| B | 100 | 3 |
|  | 50 | 0 |

We claim:

1. A heterocyclic derivative represented by the formula:

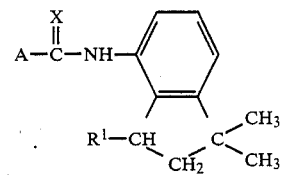

wherein $R^1$ represents a hydrogen atom or a methyl group, A represents

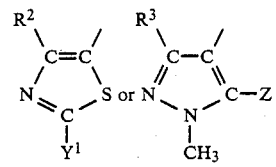

wherein $R^2$ represents a methyl group, an ethyl group or a trifluoromethyl group, $Y^1$ represents an amino group, a methyl group or a chlorine atom, $R^3$ represents a methyl group or a trifluoromethyl group and Z represents a hydrogen atom, a halogen atom or a methyl group and when A represents the formula:

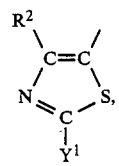

X represents an oxygen atom or a sulfur atom and when A represents the formula:

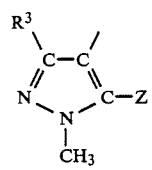

X represents a sulfur atom.

2. A fungicidal composition which comprises as an active ingredient a fungicidally effective amount of a heterocyclic derivative represented by the formula:

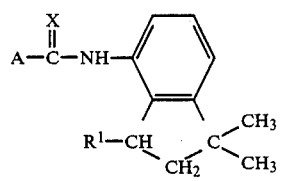

wherein $R^1$ represents a hydrogen atom or a methyl group, A represents

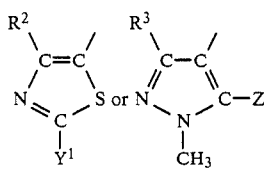

wherein R² represents a methyl group, an ethyl group or a trifluoromethyl group, Y¹ represents an amino group, a methyl group or a chlorine atom, R³ represents a methyl group or a trifluoromethyl group and Z represents a hydrogen atom, halogen atom or a methyl group and when A represents the formula:

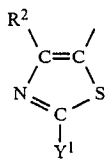

X represents an oxygen atom or a sulfur atom and when A represents the formula:

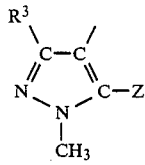

X represents a sulfur atom, and an inert carrier.

3. A method for controlling fungi which comprises applying to fungi a fungicidally effective amount of a heterocyclic compound of the formula:

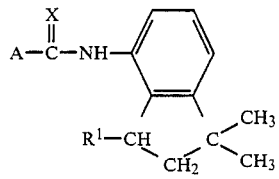

wherein R¹ represents a hydrogen atom or a methyl group, A represents

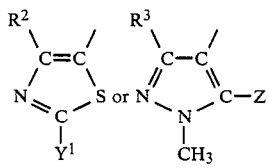

wherein R² represents a methyl group, an ethyl group or a trifluoromethyl group, Y¹ represents an amino group, a methyl group or a chlorine atom, R³ represents a methyl group or a trifluoromethyl group and Z represents a hydrogen atom, a halogen atom or a methyl group and when A represents the formula:

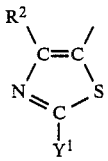

X represents an oxygen atom or a sulfur atom and when A represents the formula:

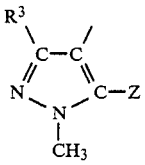

X represents a sulfur atom.

4. A method according to claim 3 wherein the fungi are a plant pathogenic fungi.

* * * * *